United States Patent [19]

Adcock et al.

[11] 4,330,475

[45] May 18, 1982

[54] AEROSOL DIRECT FLUORINATION METHOD AND APPARATUS

[76] Inventors: James L. Adcock, 7608 Queensbury Dr., Knoxville, Tenn. 37919; Ehrengard B. Renk, Department of Chemistry, University of Tennessee, Knoxville, Tenn. 37916

[21] Appl. No.: 100,761

[22] Filed: Dec. 6, 1979

[51] Int. Cl.³ .................. C07B 9/00; C07D 319/10
[52] U.S. Cl. .................. 549/380; 570/131; 570/134; 260/694; 549/369
[58] Field of Search .................. 260/694, 340.7, 340.6; 570/131, 134

[56] References Cited

U.S. PATENT DOCUMENTS

| | | | |
|---|---|---|---|
| 2,567,569 | 9/1951 | McBee et al. | 260/694 |
| 2,570,435 | 10/1951 | Downing et al. | 260/694 |
| 2,614,129 | 10/1952 | McBee et al. | 260/194 |
| 2,702,306 | 2/1955 | Gall et al. | 260/694 |
| 3,131,212 | 4/1964 | Biller | 260/694 |
| 3,480,667 | 11/1969 | Siegart et al. | 570/131 |
| 3,833,581 | 9/1974 | Mackenzie et al. | 260/694 |
| 4,187,252 | 2/1980 | Lagow et al. | 570/134 |
| 4,281,119 | 7/1981 | Lagow et al. | 260/340.6 |

OTHER PUBLICATIONS

Hackh's Chem. Dictionary, 4th Edition, pp. 168–169.

*Primary Examiner*—Ethel G. Love
*Attorney, Agent, or Firm*—Hamilton, Brook, Smith and Reynolds

[57] ABSTRACT

A method and apparatus for improving direct fluorinations are disclosed in which the material to be fluorinated is formed into an aerosol prior to fluorination.

12 Claims, 2 Drawing Figures

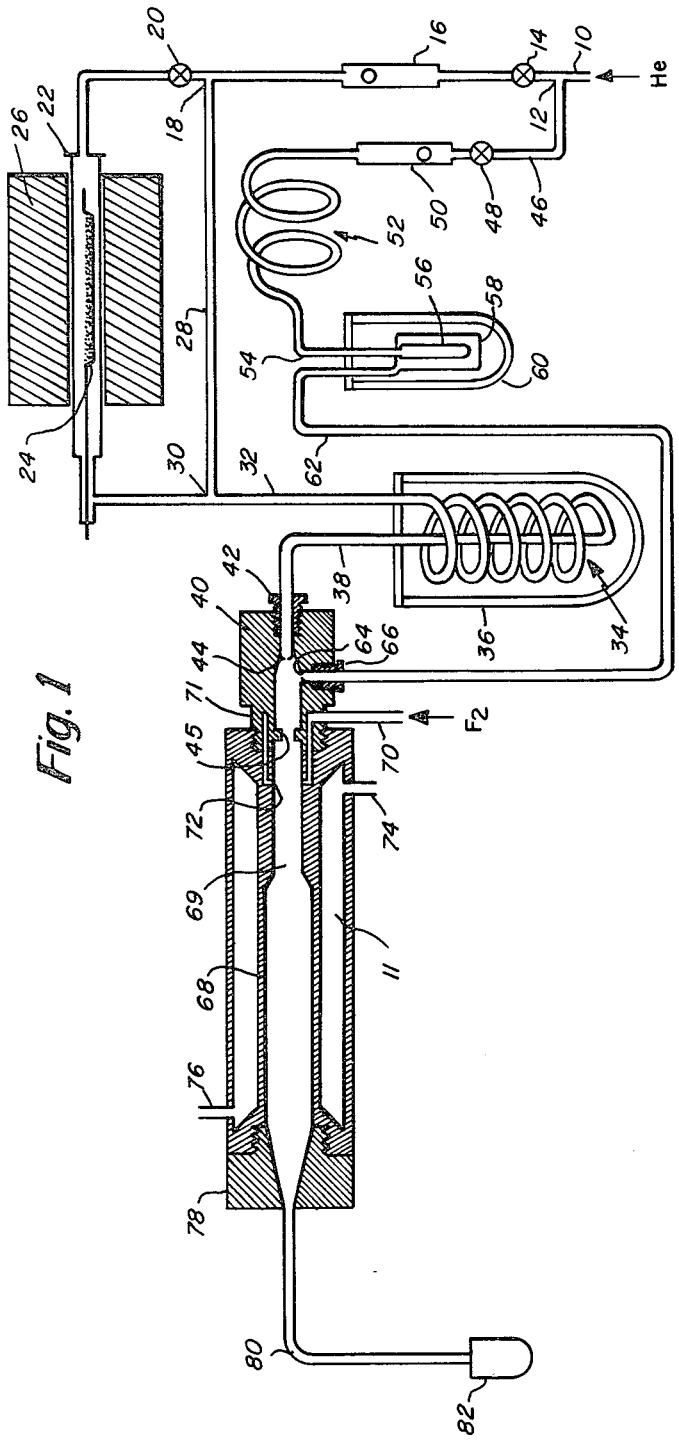

AEROSOL DIRECT FLUORINATION METHOD AND APPARATUS

DESCRIPTION

GOVERNMENT SUPPORT

Work relating to this invention was supported by the United States Navy.

TECHNICAL FIELD

This invention is in the field of fluorine chemistry, and more particularly, in the field of direct fluorination.

BACKGROUND ART

Direct fluorination of materials with fluorine gas is a highly desirable process, but prior attempts to use direct fluorination have often produced low to mediocre yields. This is because direct fluorination reactions involving elemental fluorine are characterized by quick evolution of large quantities of heat, ignition and flaming which promote product decomposition, often with explosive violence. The inability to control direct fluorination reactions so that high yields of the desired fluorinated material could be obtained has prevented direct fluorination from becoming a widely accepted method of fluorination.

One of the more promising developments in the field of direct fluorination is a process known as the La-Mar process. In this process, the material to be fluorinated is contacted with a mixture of fluorine gas and an inert gas in which the fluorine has a very low initial concentration. The concentration of fluorine is gradually increased to maintain thermodynamic and kinetic control of the reaction until the desired degree of fluorination has been achieved. See Lagow, R. J. and Margrave, J. L., "Direct Fluorination of Organic and Inorganic Substances," Proc. Natl. Acad. Sci., 67, 4, 8A (1970).

A significant extension of the La-Mar direct fluorination process is described in U.S. Pat. No. 4,113,435 issued to Lagow et al. Therein, a cryogenic zone reactor, and method for employing such a reactor, are disclosed which permit the La-Mar process to be employed in the direct fluorination of compounds which had previously been difficult to fluorinate, such as oxygen-containing compounds including ethers, esters, ketones, alcohols, and carboxylic acids.

DISCLOSURE OF THE INVENTION

This invention relates to a method of direct fluorination in which the material to be fluorinated is contained within an aerosol, and to an apparatus for carrying out such a fluorination including means to generate an aerosol of the material to be fluorinated.

In the process of this invention, an aerosol is generated which contains the material to be fluorinated. The aerosol is then flowed through the reaction zone of a fluorination reactor, such as a horizontal column reactor. A source of elemental fluorine, such as fluorine gas, is introduced into the flow of aerosol in the reaction zone under conditions sufficient for fluorination of the material to occur. Such conditions include temperature and fluorine concentration.

The apparatus for carrying out this method includes a reactor having a fluorination zone therein. Means for generating an aerosol containing a material to be fluorinated are provided as well as means for flowing the aerosol through the fluorination zone of the reactor. Finally, means for introducing a source of elemental fluorine into the fluorination zone of the reactor are also provided in the apparatus.

The method and apparatus described herein extend the capability of direct fluorination significantly and offer certain advantages over methods and apparatus previously known. One such advantage is that the process is a flow process rather than a batch process thereby providing the capability for significantly increased throughput. The method also offers extensive flexibility permitting the choice of optimum conditions of flow, temperature, and reaction rate without undue limitations arising from the physical state or volatility of the material to be fluorinated. Thus, unlike the method and apparatus of U.S. Pat. No. 4,113,435, the method disclosed herein does not rely on low temperature mass transport for maximum surface exposure to elemental fluorine. Such reliance for mass transport at low temperatures can unnecessarily slow the fluorination reaction leading to longer reaction times which limits the practical applicability of the cryogenic zone reaction process to molecules having significant vapor pressure in the solid phase.

The method and apparatus described herein also allow for the easy control of the stoichiometry of the reaction by simply varying the molar ratio of the material to be fluorinated to fluorine. This allows the product mix to be limited to a particular degree of fluorination and is particularly important where selectivity in fluorine attack is desirable.

BRIEF DESCRIPTION OF THE DRAWINGS

FIG. 1 is a schematic illustration of a fluorination apparatus according to this invention; and FIG. 2 is a partial schematic illustration of a fluorination apparatus according to this invention which apparatus has a plurality of consecutively positioned modular sections forming the fluorination zone.

BEST MODE OF CARRYING OUT THE INVENTION

The invention will now be further described with particular reference to the Figures.

In FIG. 1, helium, which serves as an inert carrier gas, is introduced into copper tubing 10 and is divided at tee 12 into two portions. The first portion flows through control valve 14 to flow meter 16 and is again divided into two portions at tee 18. Some of the helium flows through valve 20 and into furnace 22, which may be formed from stainless steel, nickel, Monel, or other resistant material. Furnace tube 22 contains a nickel boat 24 which contains between 10 and 20 grams of solid sodium fluoride which is heated between 500° C. and 900° C. by tubular heater 26. This causes the sodium fluoride in boat 24 to sublime into highly dispersed sodium fluoride particles of average radius of about 17.5 A in the helium carrier gas stream. See Espenschied, W., Matijevic, E. and Kerker, J., *J. Phys. Chem.* Ithaca, 68, 2831 (1964). These sodium fluoride particles serve as condensation nuclei for the material to be fluorinated. The helium containing the sublimated sodium fluoride is combined with that portion of helium carrier flowing in tubing 28 at mixing tee 30. Typically, only a minor portion of the helium entering tee 18 would be directed to the tube furnace 22 to avoid excessive cooling therein. The combined helium streams then flow through tubing 32 into a coil 34 located in dewar 36 containing liquid nitrogen. This chills the carrier gas and suspended sodium fluoride particles to near −196° C. The chilled helium suspension of sodium fluoride exits from dewar 36 in copper tubing 38 and enters aerosol generator 40, which may be formed from brass. Adjustable fitting 42 allows for various positions of a nozzle 44 employed to inject the helium suspension of sodium fluoride into the aerosol generator. Aerosol generator 40 contains an orifice 45 to help generate an aerosol.

The second portion of helium gas split at tee 12 flows in line 46 through valve 48 to glass flow meter 50 and through coil 52. This flow then enters glass tubing 54 which ends with fritted glass member 56 contained within a glass container 58 having therein a liquid hydrocarbon such as dioxane. The liquid hydrocarbon is vaporized by the action of the helium carrier gas bubbling out of the fritted glass member 56 and a stream of helium and vaporized hydrocarbon exit from dewar 60 in tubing 62. Dewar 60 contains a heating fluid sufficient to vaporize the hydrocarbon involved, which might be water in the case of dioxane. In the case of a volatile solid or a frozen hydrocarbon, helium in glass tube 54 flows over the solid hydrocarbon which is deposited on the walls of container 58. The helium/hydrocarbon gaseous mixture flows in line 62 into an adjustable nozzle 64 also located within aerosol generator 40 and adjustable by adjustable fitting 66. The exact position of nozzles 44 and 64 are adjusted in a precise arrangement so that the gases emitted from these nozzles meet at the natural foci. This causes the vaporized hydrocarbon injected through nozzle 64 to condense into aggregates around the sodium fluoride particles within the chilled helium carrier gas. The chilled aerosol formed is channeled into a fluorination reactor 68 formed from Monel or nickel. Fluorine gas is introduced in tubing 70, passes internally in adapter 71, and is emitted from fluorine jets 72 located circumferentially around the inner wall of the narrow flow passage of reactor 68. Fluorine introduced through jets 72 can be mixed with inert carrier gas, if desired. Efficient mixing of fluorine gas and aerosol is created by narrowed reactor zone 69.

The temperature within reactor 68 is controlled by an integral heat exchanger surrounding reactor 68 in which a heat transfer fluid, such as liquid Freon 11, is circulated by introducing it through entrance 74 and extracting it through exit 76. Fluorination occurs within the reaction zone of reactor 68 and the fluorinated products exit through narrowing adapter 78 and copper tubing 80 which directs the fluorinated materials to suitable product trap 82.

In FIG. 2, a modified version of a fluorination apparatus according to this invention is illustrated. The aerosol generation system is only partially shown and can be the same as shown in FIG. 1 or different. The initial fluorine, or stage 1 fluorine, is introduced through the internal ring of fluorine jets 72 as was the case with the apparatus of FIG. 1. The apparatus of FIG. 2 has the capability to introduce additional fluorine as well as to vary the temperature along the reaction zone.

The elongated reaction zone, added fluorination and heating and/or cooling capability are obtained by coupling consecutively positioned modular reactor sections 68a, 68b and 68c using adapters 84. Adapters 84 have an externally threaded male member on one side and an internally threaded female opening on the other side which allow the coupling of the modular sections 68a, 68b and 68c. O-rings are used to obtain proper sealing.

Adapters 84 also are designed to admit fluorine gas to the modular sections through fluorine inlets 70a, 70b and 70c. In most cases, the fluorine admitted through inlets 70a, 70b and 70c would be mixed with an inert gas such as helium and the concentration of fluorine in the mixture would increase along the reaction zone. If perfluorination is desired, the concentration of fluorine admitted to the last modular section might be 100%. Fluorine passes from the adapters 84 into staging inserts 86a, 86b and 86c, respectively. Each of the staging inserts 86a, 86b and 86c contains fluorine jets arranged in a helical pattern around the inner surface of the staging inserts.

The temperature within the modular reactor section 68a, 68b and 68c can be controlled by jacket heat exchangers each having independent coolant inlets 74a, 74b and 74c and coolant outlets 76a, 76b and 76c. Thus, each of the modular sections 68a, 68b and 68c can be cooled or heated by a circulating liquid or gas whose temperature is controlled by means of a heat exchanger device connected to a temperature-sensing device which actively senses the fluid temperature in the coolant reservoir and in the individual modular reactor sections 68a, 68b and 68c. Suitable insulation can be added, of course, to prevent heat transfer through the outer walls of the modular reactor sections.

A photochemical reactor module can be provided by directing materials in tubing 80 through transparent inert tubing 90 which is triple wrapped around used silica envelope 92 containing water-cooled mercury arc lamp 94. Products exiting from the photochemical module can then be directed to NaF trap 96 to scrub out hydrogen fluoride, to liquid nitrogen cooled trap 98 to trap fluorinated hydrocarbon and then to alumina trap 99 to absorb fluorine gas.

The method and apparatus of this invention can be used in direct fluorination of a large variety of materials. The only limitation on the materials which can be fluorinated is that the materials be capable of forming an aerosol by any technique. In regard to chemical compositions which are suitable, these include inorganic compounds; acyclic or cyclic, saturated or unsaturated, substituted or unsubstituted aliphatics; substituted or unsubstituted aromatics; heterocyclics; and polymeric materials.

The use of an aerosol in which the material to be fluorinated is present results in a very high reactant surface area for the material to be fluorinated and yet provides it with flow mobility similar to a gas. The apparatus previously described involved condensation generated aerosols, but other techniques for aerosol formation can be employed. For example, elastomeric, polymeric and other materials of low volatility could be milled at low temperature and then suspended in a gas to form a suitable aerosol for fluorination. Other researchers have reported the formation of aerosols by the reaction of gaseous components. See Pearson, R. and Langer, G., Nature, Lond., 187, 235 (1960) and Goyer, G. and Handler, G., J. Met. 12, 569 (1955).

Further, other techniques for forming aerosols are described in the technical literature, including the following: (1) "Aerosol Science", Ch. 1, Academic Press, London and New York (1966), C. N. Davis, Ed.; (2) R. D. Cadle, "Particle Size, Theory and Industrial Applications," Reinhold, N.Y. (1965); (3) G. M. Hidy, "Aerosols and Atmospheric Chemistry", Reinhold Papers Contributed Kendall Award Symposium, American Chemical Society, Los Angeles, Calif., Mar. 28–Apr. 2, 1971, Academic Press, New York and London (1972. "The Kinetics of Growth of an Aerosol in a Flow Reactor", S. Shahriari, A. N. Sarmiento and F. C. Goodrich, p. 67; (4) A. G. Sutugin, Advances in Aerosol Physics, 4, 36 (1971 translated from Russian 1973). The teachings of these references in regard to aerosol formation are incorporated herein by reference.

It should be understood, of course, that the aerosol suspension might, at some stage in the process, evaporate, reform and/or change phase, (i.e., solid←→liquid).

Important factors for controlling the degree of fluorination in the method and apparatus of this invention include temperature, ratio of material to be fluorinated to fluorine, concentration of fluorine relative to carrier flow, and reaction time.

Temperature is a very important factor in any direct fluorination. In earlier stages of a reaction, low temperatures (e.g., −60° to −70° C.) are desirable. As partial fluorination occurs, the partially fluorinated materials acquire more resistance to further attack of fluorine so that much higher temperatures can be employed towards the end of the reaction zone. Actual temperatures employed will depend upon many factors, including the material to be fluorinated, the degree of fluorination required, the specific apparatus employed, etc.

The molar ratio between the material to be fluorinated and fluorine can be easily varied in two ways. In the first, the throughput of the material to be fluorinated is varied, such as by adjusting the temperature of the hydrocarbon evaporator and the hydrocarbon carrier flow past through this reservoir as shown in FIG. 1. The variability which can be gained in this manner is illustrated in the following table for throughputs of three hydrocarbon compounds.

MASS THROUGHPUTS IN THE CURRENT REACTOR SYSTEM

Cyclohexane

| flow-rate (cc/min) | mass of hc.[a] (g/hr) | flow-rate (cc/min) | mass of hc. (g/hr) |
|---|---|---|---|
| 16 | 0.39 | 42.5 | 0.85 |
| 24 | 0.525 | 98.5 | 2.3 |
| 33 | 0.71 | 172 | 4.1 |

1,4-Dioxane

| flow-rate (cc/min) | mass of hc.[b] (g/h) | flow-rate (cc/min) | mass of hc. (g/h) |
|---|---|---|---|
| 18 | 0.1880 | 97 | 0.7596 |
| 25 | 0.2342 | 112.5 | 0.9416 |
| 42.5 | 0.2890 | 130.5 | 1.0980 |
| 58 | 0.4218 | 141 | 1.2090 |
| 72.5 | 0.4926 | 160 | 1.3614 |
| 75 | 0.5742 | 174 | 1.6206 |

Neopentane

| flow-rate (cc/min) | mass of hc.[c] (mg/h) | flow-rate (cc/min) | mass of hc. (mg/h) |
|---|---|---|---|
| 63.5 | 38.2 | | |
| 84.5 | 60.6 | 110 | 94.6 |
| 98 | 70.8 | 126 | 103.4 |
| 100 | 71.8 | 174 | 115.4 |

[a]The mass throughput of cyclohexane versus the flow-rate of helium through the hydrocarbon reservoir maintained at 30° to 31° C.
[b]The mass throughput of dioxane versus the flow-rate of helium through the hydrocarbon reservoir maintained at 34° C. is as stated above.
[c]The mass throughput of neopentane versus the flow-rate of helium through the hydrocarbon reservoir maintained at −78° C.

The molar ratio between the material to be fluorinated and fluorine can also be varied, of course, by varying the fluorine input into the fluorination reactor. As mentioned above, perfluorination usually requires an excess of fluorine.

The concentration of fluorine relative to the carrier flow is also an important factor in controlling the direct fluorinations described herein. In earlier stages of the reaction, a very low concentration of fluorine is desirable in accordance with La-Mar direct fluorination procedures. The apparatus shown in FIG. 2 allows for the convenient buildup of the concentration of fluorine by the introduction of additional fluorine into subsequent reactor modules. Since the carrier flow remains constant, this has the effect of increasing fluorine concentration. Other techniques for building up the fluorine concentration, such as the use of a semipermeable membrane to allow the carrier to pass but not the fluorine, could also result in an increase in the concentration of fluorine without any additional input of fluorine gas.

Reaction time is also an important factor in determining the degree of fluorination obtained. This is a function of the length of the reactor and the volume of flow through the reactor. The flow in the reactors described in FIGS. 1 and 2 is largely determined by the carrier flow. In general, it is necessary to keep this flow high enough to form an aerosol, but low enough to get a sufficiently long reaction time. Once the materials are trapped in the product trap, the reaction is virtually stopped. The length of the reactor, and thus the reaction time, can be successfully increased by adding a coil formed from copper or other fluorine resistant materials to any length desired at the end of the reactor system. This coil can be maintained at any desired temperature.

The invention is further specifically illustrated by the following examples.

EXAMPLE 1

Aerosol Fluorination of Cyclohexane

The reaction was carried out in a one-stage reactor as illustrated in FIG. 1.

The tube furnace was heated to 800° C. to sublime sodium fluoride from 20 grams of sodium fluoride placed in the boat. A carrier flow of 3.8 L/min helium containing sodium fluoride particles in suspension was chilled to about −196° C. in a liquid-nitrogen dewar and fed into the aerosol generator, which was held at 30° C.

Cyclohexane (0.85 g/hr, 10 mmoles/hr) was reacted with fluorine (16 cc/min, 40 mmoles/hr) diluted with 100 cc/min helium. The reactor was cooled to −60° C. In a two hour run, approximately one gram of crude product was collected. The crude product consisted of a mixture of oil and solid. Water and hydrogen fluoride were removed by treating the crude product with sodium fluoride and L-4A molecular sieves. GLC separation of the crude product gave 190 mg monofluorocyclohexane (26%; identified by IR and MS); 150 mg of a mixture of different isomers of difluorocyclohexane (20%; identified by MS) and some highly fluorinated materials. 155 mg of cyclohexane (21%) were recovered unreacted.

EXAMPLE 2

Aerosol Fluorination of Dioxane in One-Stage Reactor

The reaction was carried out in a one-stage reactor as illustrated in FIG. 1 and the tube furnace was heated to 800° C. to sublime sodium fluoride. A carrier flow of 5 L/min helium containing sublimed sodium fluoride was chilled to about −196° C. in a dewar and fed into the aerosol generator which was heated to 40° C. to avoid condensation of hydrocarbon on the walls of the generator. The reactor was cooled to −60° C. Dioxane (0.88 g/hr, 10 mmoles/hr) was reacted with fluorine (96 cc/min, 240 mmoles/hr). In a two hour run, 1.33 g of crude product were obtained. Water and hydrogen fluoride were removed by treatment with sodium fluoride and L-4A molecular sieves. GLC separation of 314.4 mg of crude product gave 121.6 mg (39%) of a mixture of two different isomers of tetrafluorodioxane. Small quantities of several higher and lower fluorinated materials were also obtained.

EXAMPLE 3

Aerosol Fluorination of 1,4-dioxane In a Four-Stage Reactor

The reaction was carried out in a four-stage reactor as illustrated in FIG. 2. The tube furnace was heated to 800° C. A carrier flow of 0.4 L/min helium containing suspended sodium fluoride was chilled and fed into the aerosol generator, which was maintained at 40° C. The first module was cooled to −65° C., the second to −30° C., and the third to 0° C. by means of thermocouple actuated solenoid valves on coolant outlets $76a$, $76b$ and $76c$ which control independently the flow of sufficient circulating −65° C. Freon 11 coolant through each heat exchanger jacket to maintain each pre-set temperature. A 10 meter $\frac{3}{8}$" standard refrigeration copper coil kept at room temperature and a 15 meter copper coil heated to 45° C. were added following module $68c$ of the reactor system. 1,4-dioxane (0.088 g/hr, 1 mmole/hr) was reacted with fluorine (overall 200 cc/min, 480 mmoles/hr; 20 cc/min, 48 mmoles/hr in stage 1 and stage 2; 60 cc/min, 144 mmoles in stage 3; 100 cc/min, 240 mmoles in stage 4). In a two hour run 170 mg of crude product were collected. Water and hydrogen fluoride were removed by treating the crude product with sodium fluoride and L-4A molecular sieves. GLC separation of the crude product gave 13.3 mg perfluorodioxane (7.8%), 20.7 mg 2-hydryl-F-1,4-dioxane (12.2%), 29.4 mg dihydryl-F-1,4-dioxane (17.3%), besides penta- and tetra- fluoro-1,4-dioxanes (each was identified by comparison with authentic samples).

EXAMPLE 4

Aerosol Fluorination of Neopentane

The reaction was carried out in the four-stage reactor as shown in FIG. 2. The tube furnace was heated to 800° C. A carrier flow of 0.41 L/min helium containing sodium fluoride particles were chilled and fed into the aerosol generator which was kept at 15° C. The first module was cooled to −60° C., the second to −30° C. and the third to 0° C. A 10 meter $\frac{3}{8}$" copper coil added following module $68c$ of the reactor system was heated to 45° C. Neopentane (0.72 g/hr, 1 mmole/hr) was reacted with fluorine (overall 200 cc/min, 480 mmoles/hr; 20 cc/min, 48 mmoles/hr in stage 1 and 2; 60 cc/min, 144 mmoles/hr in stage 3 and 100 cc/min, 240 mmoles in stage 4). In a two hour run 310 mg of crude product were collected. Water and hydrogen fluoride were removed by treating the crude product with sodium fluoride and L-4A molecular sieves. GLC separation of the crude product gave 28.5 mg perfluoroneopentane (9.2%), 74.4 mg monohydryl-F-neopentane (24%), 101 mg dihydryl-F-neopentane besides tri- and tetrahydryl-F-neopentanes 1 (each was identified by comparison with authentic samples).

Industrial Applicability

This invention has industrial applicability in the direct fluorination of materials to produce fluorinated compositions having utility as lubricants, heat transfer media, solvents, plasticizers, waxes, sealing liquids, refrigerants, surface active agents, oil and water repelling agents, inert solvents, diluents, monomers for preparing valuable fluoropolymers, and many other utilities.

Equivalents

Those skilled in the art will recognize or be able to ascertain using no more than routine experimentation many equivalents to the specific embodiments of the invention described herein. For example, other materials of construction, carrier gases, sources of elemental fluorine, etc., could be used. Such equivalents are intended to be encompassed by the following claims.

We claim:

1. A process for fluorinating a material, comprising:
   a. generating an aerosol containing the material to be fluorinated by forming a colloidal suspension of solid carrier particles in an inert gas and subsequently condensing the material to be fluorinated onto said carrier particles;
   b. flowing said aerosol through the reaction zone of a fluorination reactor; and,
   c. introducing elemental fluorine into the flow of said aerosol under conditions sufficient for fluorination of said material to occur.

2. A process of claim 1 wherein said elemental fluorine is introduced by flowing fluorine gas into the reaction zone of said fluorination reactor.

3. A process of claim 2 wherein the concentration of fluorine gas is increased along the flow path of said aerosol through the reaction zone of said fluorination reactor.

4. A process of claims 1, 2 or 3 wherein the temperature is raised along the flow path of said aerosol through the reaction zone of said fluorination reactor.

5. A process of claim 4 wherein said inert gas comprises helium.

6. A process of claim 5 wherein said carrier particles comprise sodium fluoride particles.

7. A process of claim 6 wherein the material to be fluorinated comprises a hydrocarbon compound.

8. A process of claim 7 wherein said hydrocarbon compound comprises cyclohexane.

9. A process of claim 7 wherein said hydrocarbon comprises dioxane.

10. A process of claim 7 wherein said hydrocarbon comprises neopentane.

11. In a direct fluorination process wherein a material to be fluorinated is contacted with elemental fluorine under conditions sufficient to produce fluorination of said material:

The improvement comprising generating an aerosol of the material to be fluorinated by forming a colloidal suspension of solid carrier particles in an inert gas and subsequently condensing the material to be fluorinated onto said carrier particle and thereafter contacting said aerosol with elemental fluorine.

12. The improvement of claim 11 wherein said elemental fluorine comprises fluorine gas.

* * * * *